US005569026A

United States Patent [19]

Novak

[11] Patent Number: 5,569,026
[45] Date of Patent: Oct. 29, 1996

[54] TUBE PUMP IN WHICH TUBE CAN BE INSERTED ONLY IN ONE DIRECTION

[75] Inventor: Pavel Novak, Schaffhausen, Germany

[73] Assignee: Storz Endoskop GmbH, Schaffhausen, Germany

[21] Appl. No.: 377,223

[22] Filed: Jan. 24, 1995

Related U.S. Application Data

[63] Continuation-in-part of Ser. No. 77,770, Jun. 18, 1993, abandoned.

[30] Foreign Application Priority Data

Jun. 18, 1992 [DE] Germany ............................ 9208212 U

[51] Int. Cl.⁶ .................................................... F09B 43/08
[52] U.S. Cl. .................................... 417/477.1; 417/477.2; 604/153
[58] Field of Search .................................... 417/474, 476, 417/477.1, 477.2; 604/151, 153

[56] References Cited

U.S. PATENT DOCUMENTS

| | | | |
|---|---|---|---|
| 4,537,561 | 8/1985 | Xanthopoulos | 417/477.2 |
| 4,559,040 | 12/1985 | Horres et al. | 604/153 |
| 4,585,399 | 9/1986 | Baier | 417/477 |
| 4,671,792 | 6/1987 | Borsanyi | 604/153 |
| 5,057,081 | 10/1991 | Sunderland | 604/153 |
| 5,201,711 | 4/1993 | Pasqualucci et al. | 604/153 |
| 5,213,483 | 5/1993 | Flaherty et al. | 417/477 |
| 5,242,279 | 9/1993 | Knuth | 417/474 |

*Primary Examiner*—Peter Korytnyk
*Attorney, Agent, or Firm*—Antonelli, Terry, Stout & Kraus

[57] ABSTRACT

A tube pump for conveying liquid or viscous media, with a pump head on which at least two pump rollers are arranged which latter can act in succession on a tube, carrying the medium to be conveyed and located in the tube bed, in such a way that the medium is transported by squeezing the tube tightly, wherein the tube bed and the tube are fashioned so that the tube can be inserted in the tube bed in only one direction. This can be achieved by using end pieces of differing geometric forms and/or sizes, and/or providing that one end piece is magnetic and providing a magnetic sensor in the corresponding socket of the tube bed.

6 Claims, 2 Drawing Sheets

TUBE PUMP IN WHICH TUBE CAN BE INSERTED ONLY IN ONE DIRECTION

CROSS REFERENCE TO RELATED APPLICATION

This application is a continuation-in-part application of prior application Ser. No. 08/077,770, filed Jun. 18, 1993, now abandoned.

SPECIFICATION

BACKGROUND OF THE INVENTION

The invention relates to a tube pump.

Rotary or tube pumps are very frequently utilized in medical technology for the pumping of blood, blood substitute fluids and/or irrigation fluids. The conventional tube pumps for the conveying of liquid or viscous media exhibit a pump head on which at least two pump rollers are arranged which can be made to act in succession on a tube, wherein the medium to be conveyed is provided and which is located in a tube bed, in such a way that the medium is transported by squeezing the tube tightly.

In this process, it is usually very important to insert the pump hose in the pump head in such a way that the pumping direction is correct since otherwise life-threatening conditions can arise for the patient, for example by infusion of air which can lead to air embolism and/or by suction drainage of blood or other body fluids.

The danger of an inadvertent erroneous insertion of the pump hose is especially acute in simple systems inasmuch as a corresponding tube guidance (e.g. dialysis devices) cannot prevent a reversed insertion of the tube kit so that thus the correct pumping direction is not observed. Normally, merely an arrow is provided at the pump head or in its proximity which is to ensure the correct insertion. Unfortunately, in clinical practice, this is frequently inadequate.

SUMMARY OF THE INVENTION

The invention is based on the object of further developing a tube pump of this type in such a way that an insertion of the tube leading to a pumping direction in opposition to the desired direction is impossible.

According to the invention, the tube bed and the tube are fashioned so that the tube can be inserted in the tube bed only in one direction. This can be achieved, for example, in an especially simple way by providing that the tube has differently large end pieces which latter can be inserted only in one combination possibility in adapted sockets in the tube bed and/or by providing that at least one end piece of the tube of a magnetic material and providing a magnetic sensor in the corresponding socket of the tube bed.

Moreover, at least one of the end pieces can be provided with additional coding, for example with a groove.

DETAILED DESCRIPTION OF THE PREFERRED EMBODIMENTS

According to the invention, the end pieces 1, 2 of the tube segment 3, which are inserted in the pump head and serve for fixation of the tube, are fashioned in such a way that a confusion of the direction becomes impossible.

Figure 1:
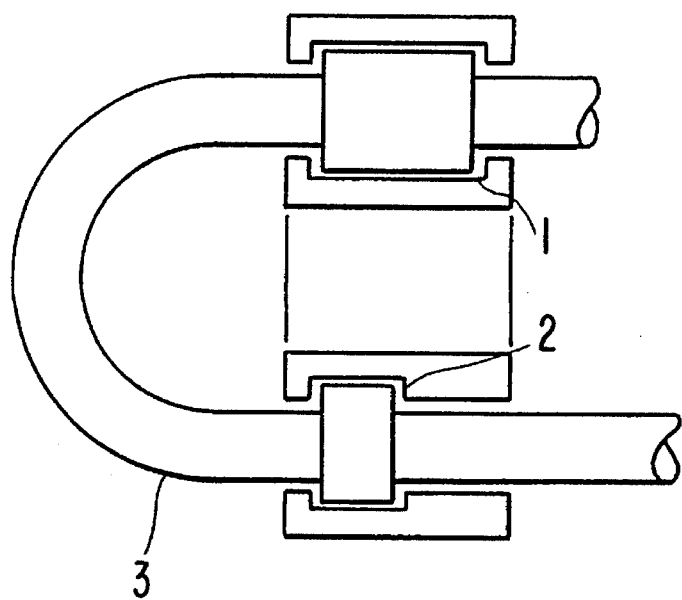
FIG. 1 shows a portion of a tube pump.

This can be attained, as illustrated in FIG. 1, in a simple way by designing the two end pieces 1, 2 to be of different sizes, for example of differing length, so that, in case of a wrong insertion of the tube kit in the locating elements of the tube pump, one of the end pieces cannot be fitted into the corresponding sockets of the tube pump.

Figure 3:
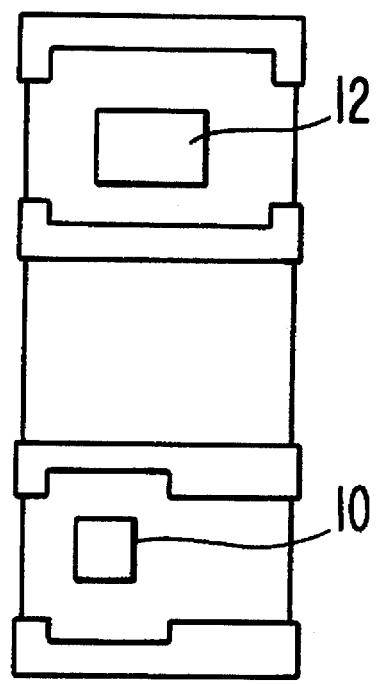
FIG. 3 shows the use of sensors provided in the sockets.

As an alternative or in addition to use of end pieces 1, 2 of differing sizes, at least one end piece may be made of or provided with a magnetic material, and the corresponding socket provided with a magnetic sensor 10 (see FIG. 3). For example, one of the tube end pieces may be made of a magnetic material and the corresponding socket provided with a magnetic sensor 10. The sensor 10 can detect whether the tube is inserted correctly or incorrectly, thereby preventing incorrect insertion, e.g., by sounding an alarm or preventing operation if incorrect insertion is detected.

Figure 2:
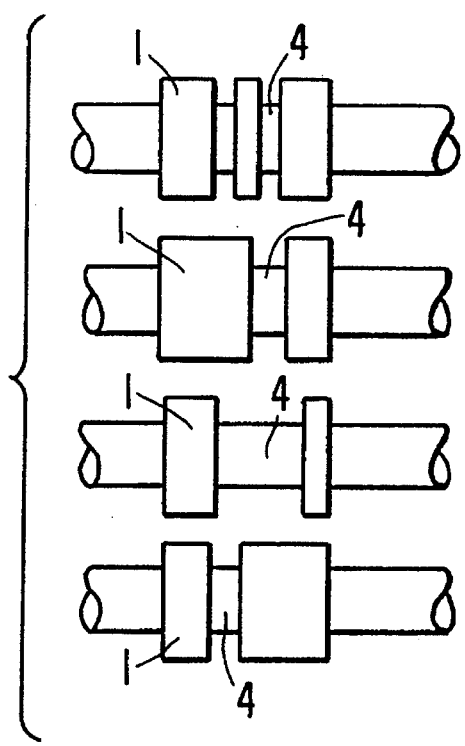
FIG. 2 shows various differently coded end pieces.

As shown in FIG. 2, an additional coding of the tube kit can be realized by adding at least one indentation and, in particular, a continuous groove 4 at one of the end pieces, preferably the larger one 1 of the two end pieces.

This is advantageous in all those instances when, for example, a device includes tube kits with different pump tube segment diameters for the pumping of varying amounts of liquid, wherein differing operating parameters are to be settable in correspondence with the tube kit utilized.

In this way, the device can make available to the operator the correct setting range, automatically and without chance of confusion, which pertains to the respectively used tube kit, so that erroneous operations are avoided.

The automatic identification of the indentation or notch mentioned in the foregoing can be realized by a sensor 12 (see FIG. 3) either optically (e.g. a light barrier) or mechanically (a correspondingly designed microswitch).

What is claimed:

1. A tube pump, comprising:
   a tube for conveying liquid or viscous medium therethrough, the tube including two end pieces, wherein each of the end pieces has a cylindrical geometric form, one of the end pieces being larger than another of the end pieces; and wherein at least one of the end pieces exhibits an additional coding in the form of at least one continuous groove;
   a tube bed having a pair of sockets, one of the sockets being larger than another of the sockets, whereby the end pieces can be installed in the sockets in only one possible combination;
   a sensor provided in at least one of the sockets for identifying the additional coding of at least one of the end pieces; and
   a pump head on which at least two pump rollers are arranged, the pump rollers acting in succession on and squeezing the tube to convey the medium therethrough in one direction.

2. A tube pump according to clam 1, wherein at least one of the end pieces comprises a magnetic material and wherein at least one of the sockets is provided with a magnetic sensor for detecting if the end piece comprising the magnetic material is installed therein.

3. A tube pump according to claim 1, wherein the sensor is an optical sensor for identifying the additional coding and wherein different operating parameters of the tube pump are settable in correspondence with the additional coding identified.

4. A tube pump according to claim 3, wherein the optical sensor is a light barrier.

5. A tube pump according to claim 1, wherein the sensor is a mechanical sensor for identifying the additional coding and wherein different operating parameters of the tube pump are settable in correspondence with the additional coding identified.

6. A tube pump according to claim 5, wherein the mechanical sensor is a microswitch.

* * * * *